(12) United States Patent
Huh et al.

(10) Patent No.: US 11,920,116 B2
(45) Date of Patent: *Mar. 5, 2024

(54) SYSTEMS AND METHODS FOR PRODUCING MICRO-ENGINEERED MODELS OF THE HUMAN CERVIX

(71) Applicant: THE TRUSTEES OF THE UNIVERSITY OF PENNSYLVANIA, Philadelphia, PA (US)

(72) Inventors: Dongeun Huh, Villanova, PA (US); Jeongyun Seo, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/352,015

(22) Filed: Jun. 18, 2021

(65) Prior Publication Data

US 2022/0010255 A1    Jan. 13, 2022

Related U.S. Application Data

(63) Continuation of application No. 15/769,387, filed as application No. PCT/US2016/058220 on Oct. 21, 2016, now Pat. No. 11,066,633.

(60) Provisional application No. 62/244,963, filed on Oct. 22, 2015.

(51) Int. Cl.
| | |
|---|---|
| *C12M 1/12* | (2006.01) |
| *C12M 3/00* | (2006.01) |
| *C12M 3/06* | (2006.01) |
| *C12N 5/071* | (2010.01) |

(52) U.S. Cl.
CPC ............ *C12M 25/02* (2013.01); *C12M 21/08* (2013.01); *C12M 23/16* (2013.01); *C12N 5/0682* (2013.01); *C12N 2502/1347* (2013.01); *C12N 2502/243* (2013.01); *C12N 2502/28* (2013.01); *C12N 2513/00* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 2011/0212501 A1* | 9/2011 | Yoo ..................... | C12M 25/14 427/337 |
| 2014/0093905 A1* | 4/2014 | Ingber ................. | G01N 33/5091 435/287.1 |

* cited by examiner

*Primary Examiner* — Teresa E Knight
(74) *Attorney, Agent, or Firm* — BakerHostetler

(57) ABSTRACT

The presently disclosed subject matter provides systems and methods for producing a three-dimensional model of a human cervix. A microdevice is provided for culturing human cervical cells. The microdevice can include an upper microchannel including live ectocervical epithelial cells. The microdevice can include a lower microchannel including a first parallel lane and a second parallel lane including stromal media. The first and the second parallel lanes can be lined with live vascular endothelial cells. The lower microchannel can include a third parallel lane including uterine fibroblasts and live smooth muscle cells embedded in hydrogel. The first, second, and third lanes of the lower microchannel can be separated by protrusion structures. The third parallel lane can be positioned in the lower microchannel in between the first and the second parallel lanes. The microdevice can further include a porous membrane positioned in between the upper microchannel and the lower microchannel.

13 Claims, 9 Drawing Sheets

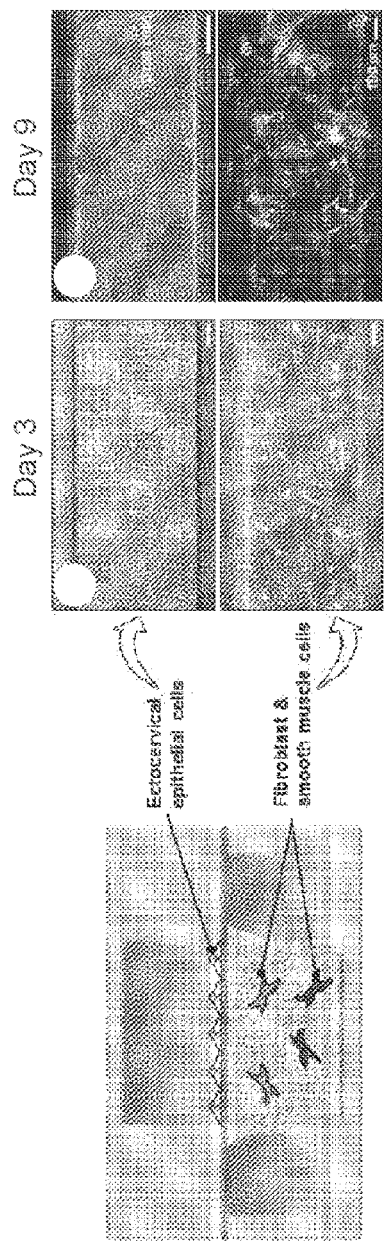
Figure 5
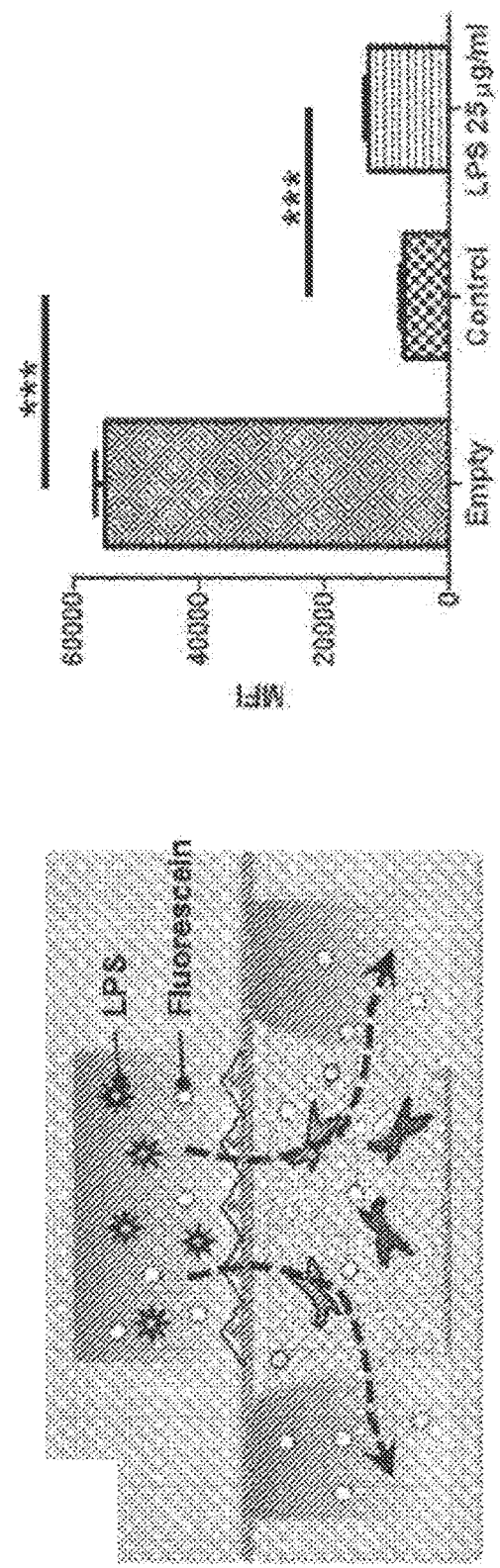
Figure 6A
Figure 6B

SYSTEMS AND METHODS FOR PRODUCING MICRO-ENGINEERED MODELS OF THE HUMAN CERVIX

CROSS REFERENCE TO RELATED APPLICATION

This application is related to, and claims priority from, Provisional Patent Application No. 62/244,963, entitled "Systems And Methods For Producing Micro-Engineered Models Of The Human Cervix," which was filed on Oct. 22, 2015, the entire contents of which is incorporated by reference herein.

BACKGROUND

Certain methods for investigating cellular and tissue functions in the human cervix and for mechanistic studies on development and progression of pathological conditions have used animal models of the cervix. However, animals used in certain studies are considerably divergent from humans in their genetic backgrounds, organ architecture, cellular compositions and functions, and local microenvironment of the cervix. Transwell-based in vitro cervical models have also been proposed as alternatives to animals, but these two dimensional models that are based on culture of living cervical cells in static conditions are greatly limited in their ability to recapitulate the complex three-dimensional structure of the cervix and the dynamic mechanical and biochemical microenvironments that play an essential role in physiology and pathology of the cervix. Thus, there is a need for a platform to support a three-dimensional cell culture in a single device to replicate tissue compartmentalization in the human cervix.

SUMMARY

Systems and methods for producing micro-engineered models of the human cervix are disclosed herein. In an example embodiment, a microdevice is provided for culturing human cervical cells. The microdevice can include an upper microchannel including live cervical epithelial cells. The microdevice can include a lower microchannel that contains three parallel lanes—a first central lane and second and third side lanes. The first lane can be separated by protrusion structures from the second and third side lanes. The first lane is used for cervical stromal formation by including fibroblasts and smooth muscle cells in hydrogel, and the second and third lanes can be used for flowing stromal media. The second and third parallel lanes can be lined with live vascular endothelial cells to form vasculature. The microdevice can further include a porous membrane positioned in between the upper microchannel and the lower microchannel.

In some embodiments, the porous membrane can be configured to pass nutrients, oxygen, growth factors, cytokines, chemokines, pathogens, particulates, chemicals, and drug compounds from the upper microchannel to the lower microchannel (or vice versa).

In some embodiments, the upper microchannel and the lower microchannel can have separate inlets and outlets through which materials can be injected into the microdevice.

In some embodiments, the second and third side parallel lanes in the lower microchannel can include separate inlets and outlets to apply biochemical and pressure gradients across the first lane.

In some embodiments, the protrusion structures can be configured to pin the menisci of a hydrogel precursor solution injected into the first parallel lane of the lower microchannel and prevent the hydrogel precursor from spilling into the second and third parallel lanes.

In some embodiments, the live cervical epithelial cells in the upper microchannel can be perfused with epithelial media. The live cells in the lower microchannel can be perfused with the stromal media in the second and third parallel lanes and/or directly through the hydrogel in the first lane.

According to another aspect of this disclosure, a method of manufacturing a microdevice for culturing human cervical cells is provided. Hydrogel precursor solution including cervical stromal cells can be injected into an air-filled center lane of a lower microchannel of the microdevice. Human cervical epithelial cells can be injected into an upper microchannel of the microdevice, resulting in an extracellular membrane coated surface of at least one epithelial monolayer. A first side channel and a second side channel of the lower microchannel can be perfused with stromal media. Vascular endothelial cells can be seeded into the first side channel and the second side channel to form a lining of endothelial cells.

In some embodiments, live cervical epithelial cells can be injected into the first side channel and/or the second side channel to form a lining of epithelial cells directly adjacent to the hydrogel construct in the center lane. Vascular endothelial cells can be seeded into the upper microchannel of the microdevice, resulting in the formation of a vascular endothelial monolayer on the membrane surface.

In some embodiments, live cervical epithelial cells can be injected into the first side channel to form a lining of epithelial cells immediately adjacent to the hydrogel construct in the center lane. Vascular endothelial cells can be injected into the second side channel to form a lining of endothelial cells immediately adjacent to the hydrogel construct in the center lane.

In some embodiments, vascular endothelial cells can be embedded in the hydrogel in the center lane to form perfusable vascular tubes. Perfusion through these vessels can be achieved by applying pressure gradients across the hydrogel layer between the first side channel and the second side channel.

In some embodiments, the hydrogel precursor solution injected into the center lane can be allowed to solidify into a hydrogel before injecting the human cervical epithelial cells into the upper microchannel.

In some embodiments, the hydrogel precursor solution injected into the center lane can be allowed to solidify into a hydrogel before injecting the human cervical epithelial cells into the side lanes in the lower microchannel.

In some embodiment, the disclosed microdevice can allow for co-culture of human cervical epithelial cells, fibroblasts, smooth muscle cells, endothelial cells, immune cells, and other cervical cells. The disclosed biomimetic microsystem can make it possible to faithfully recapitulate complex and dynamic interplay between multiple tissue types within the cervix and to mimic, directly visualize, and quantitatively analyze structural and functional alterations of the cervix during pregnancy and various other physiological and pathological processes.

The disclosed subject matter can have a wide variety of applications including use as a research tool for biochemical and mechanical investigation of various biological processes in the cervix and also offer an innovative screening platform for identification of new therapeutic targets and development of drugs and treatment strategies. The disclosed microdevice can provide new opportunities to develop personalized human disease models that use patient-derived cells to simulate patient-specific disease processes. The disclosed microdevice can also be used to develop screening platforms capable of simulating and predicting physiological responses of the human cervix to pharmaceuticals, chemicals, environmental toxins, and consumer products. The disclosed microdevice can also be used to test safety and effectiveness of medical devices used for vaginal inspection and treatment.

BRIEF DESCRIPTION OF THE DRAWINGS

FIG. 5 shows images of ectocervical epithelium and uterine fibroblasts at different stages of the cell culture process in accordance with the disclosed subject matter.

FIG. 6A shows an image of the exemplary microdevice introduced with lipopolysaccharides to simulate a bacterial infection in the cervix in accordance with the disclosed subject matter.

FIG. 6B shows a graph of the results of the simulated bacterial infection in the microdevice in accordance with the disclosed subject matter.

Figure 1:
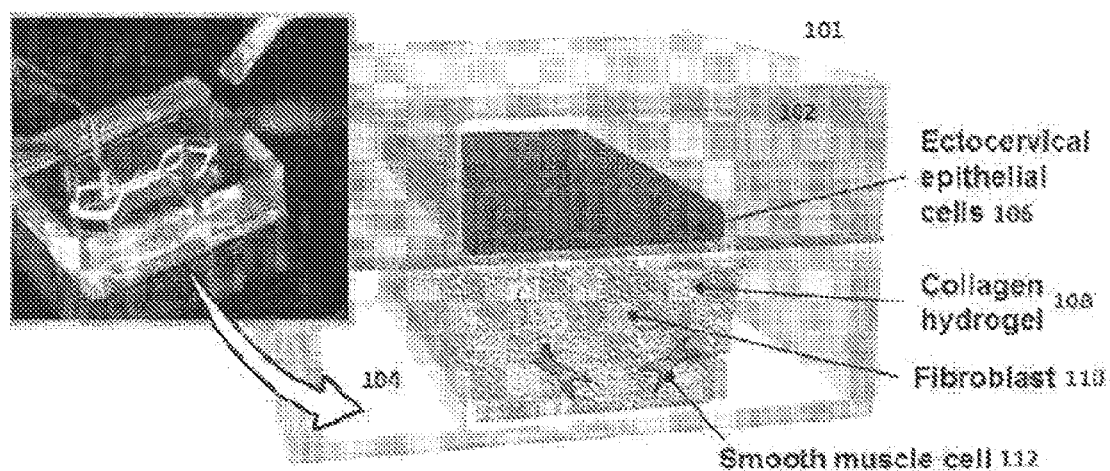
FIG. 1 shows a diagram of an exemplary microdevice modelling a cervical microsystem in accordance with the disclosed subject matter.

Throughout the drawings, the same reference numerals and characters, unless otherwise stated, are used to denote like features, elements, components or portions of the illustrated embodiments. Moreover, while the disclosed subject matter will now be described in detail with reference to the figures, it is done so in connection with the illustrative embodiments.

DETAILED DESCRIPTION OF EMBODIMENTS

The subject matter disclosed herein provides systems and methods for producing micro-engineered models of the human cervix. The subject matter disclosed herein includes a compartmentalized three-dimensional microfluidic device, hereinafter also referred to as a microdevice, for physiological long-term culture of human cervical cells.

In some embodiments with reference to FIG. 1, an exemplary microdevice 101 modelling a cervical microsystem can include an upper channel 102 lined with a monolayer of live human cervical epithelial cells 106. The microdevice 101 can also include a lower channel 104 underneath the upper channel 102. In the lower channel 104, cervical fibroblasts and smooth muscle cells can be embedded in a micropatterned hydrogel 108. Such a "human cervix-on-a-chip" model provided by the microdevice 101 can mimic the cervical epithelium supported by the fibromuscular stroma in the human cervix. The upper channel 102 can culture the live human cervical epithelial cells 106 while the lower channel 104 can be used to mimic the stromal tissue of the human cervix. Nutrients to the cervical epithelial cells 106 can be provided through inlets in the upper channel 102 and waste can be removed from similar outlets as well. Nutrients to the cells in the lower channel 104 can be provided through inlets in the lower channel 104 and waste from the lower channel 104 can be collected from outlets in the lower channel 104.

In some embodiments, live cervical epithelial cells can be injected in the side channels of the lower microchannel to form epithelial monolayers immediately adjacent to the cell-laden hydrogel in the center lane. The epithelial cells can be maintained by flowing epithelial media through the side channels. Vascular endothelial cells can be seeded into the upper channel and/or cultured on the surface of the membrane to mimic a stromal-vascular interface in the cervix, resulting in the formation of a vascular endothelial monolayer on the membrane surface.

In some embodiments, live cervical epithelial cells and vascular endothelial cells can be injected in the first side channel and the second side channel of the lower microchannel, respectively to integrate multiple tissue types within a single layer of the microdevice. In some embodiments, live cervical epithelial cells and vascular endothelial cells can be injected in the first side channel and the second side channel to form a lining of epithelial cells adjacent to the hydrogel construct in the center lane.

In some embodiments, vascular endothelial cells can be included in the hydrogel layer to induce vasculogenesis and form a network of perfusable blood vessels. Flow through the vessels can be generated by applying a pressure gradient across the hydrogel.

Figure 2:
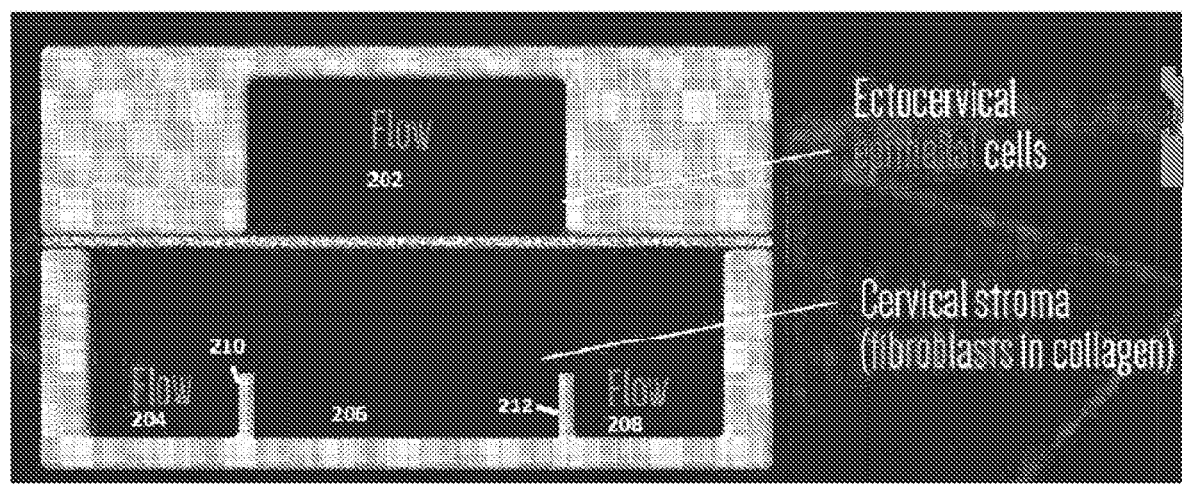
FIG. 2 shows another diagram of an exemplary microdevice modelling a cervical microsystem in accordance with the disclosed subject matter.

FIG. 2 shows another diagram of the microdevice 101 shown in FIG. 1. As shown in FIG. 2, the structure of microdevice 101 allows for nutrients and waste to flow in the upper channel 202, which corresponds to the upper channel 102 of FIG. 1. Similarly, parallel side channels 204 and 208 of the lower channel can support flow of nutrients, waste, and other materials. Parallel side channels 204 and 208 of the lower channel can be positioned adjacent to the center parallel lane 206 of the lower microchannel in which cervical stroma can be cultured. Protrusion structure 210 can separate the parallel side channel 204 from the center lane 206 of the lower microchannel and protrusion structure 212 can separate the parallel side channel 208 from the center lane 206. Protrusion structures 210 and 212 can prevent the cervical stroma, hydrogel solution 108, fibroblasts 110, and smooth muscle cells 112 from spilling over into the side channels 204 and 208 which contain transport streams of biomaterials needed to support the cervical stroma in center lane 206.

Figure 3:
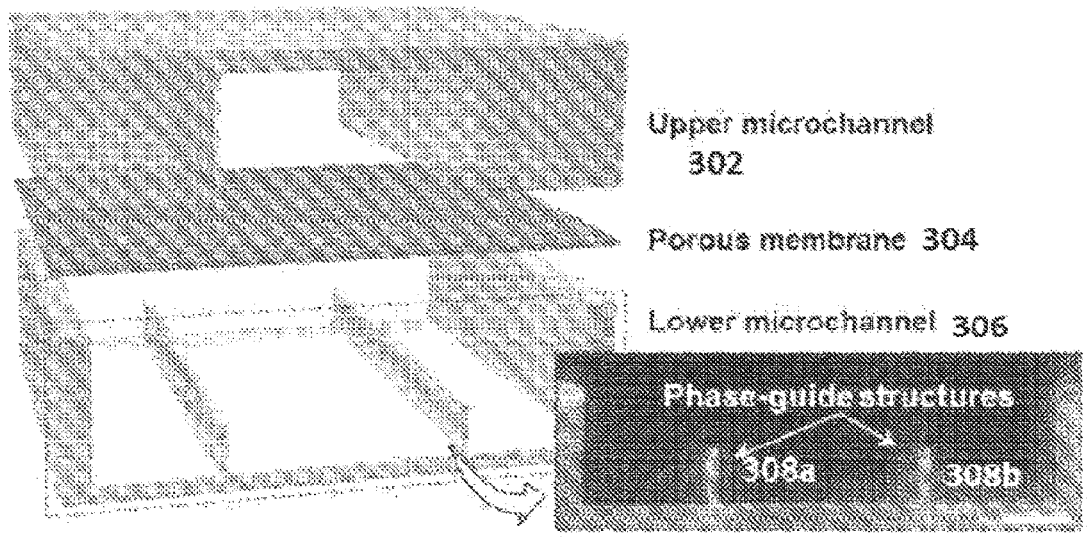
FIG. 3 shows a diagram of an exemplary structure of the microdevice used to model a cervical microsystem before it is injected with biomaterials in accordance with the disclosed subject matter.

FIG. 3 shows a diagram of an exemplary structure of the microdevice 101 of FIGS. 1 and 2 before it is injected with biomaterials. A porous membrane 304 can be positioned between the upper microchannel 302 and lower microchannel 304. The porous membrane 304 can be a thin, optically transparent porous membrane. The porous membrane can be composed of polymer. Additionally and/or alternatively, the porous membrane 304 can be a biomaterial that is composed of one or more of a hydrogel, ex vivo membranes isolated from human and/or animal tissues/organs, and/or a decellularized extracellular matrix (ECM) prepared from human and/or animal tissues/organs. According to an exemplary implementation, the porous membrane 304 can be composed of polyester. The microfabricated protrusion structures 308a and 308b at the bottom floor of the lower microchannel 306, which correspond to protrusion structures 210 and 212 of FIG. 2, can separate the lower microchannel 306 into three parallel lanes. These "phase-guide" like structures can be used to enable formation and spatial confinement of a cell-laden hydrogel layer in the center lane.

Figures 4A, 4B, 4C:
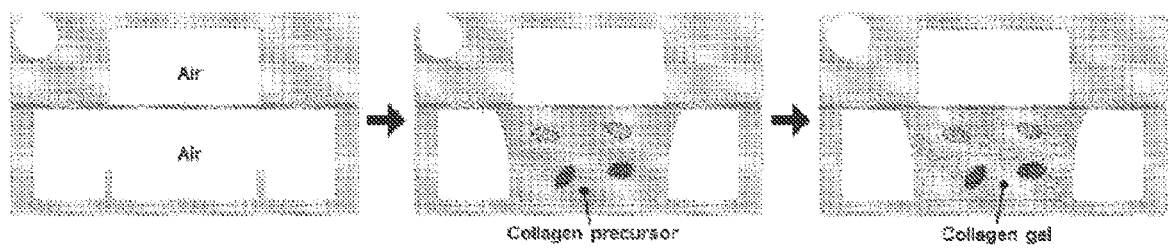
FIGS. 4A-4E show an exemplary process for forming the epithelial and stromal layers in an exemplary microdevice for culturing human cervical cells in accordance with the disclosed subject matter.
Figures 4D, 4E:
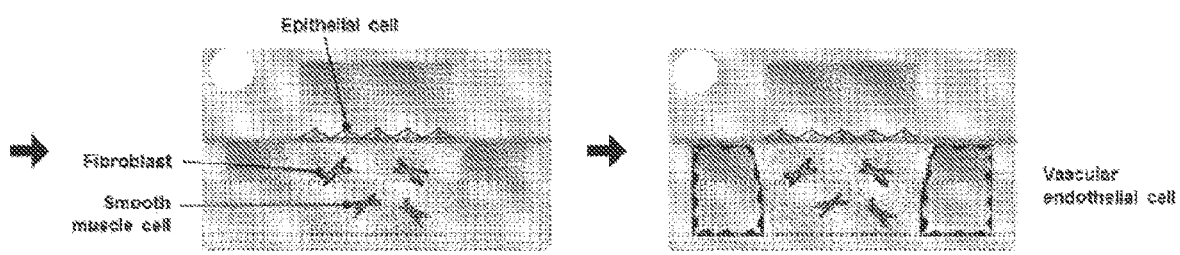

FIGS. 4A-E shows an exemplary process for forming the epithelial and stromal layers in an exemplary microdevice 101 for culturing human cervical cells. As illustrated in FIG. 4A, the upper microchannel and the lower microchannel can be filled with air at the start of the fabrication process as shown in FIG. 3. As illustrated in FIG. 4B, hydrogel precursor solution including cervical stromal cells and hydrogel precursor can be injected into an air-filled center lane of a lower microchannel of such a hollow microfluidic structure. When a hydrogel precursor solution containing cervical stromal cells is injected into the air-filled center lane of the lower chamber, its menisci can be pinned at these phase-guide structures due to surface tension, preventing spillage of the solution into the two side lanes during gelation, as illustrated in FIG. 4C. As illustrated in FIG. 4D, human cervical epithelial cells can be injected into an upper microchannel of the microdevice and can be allowed to attach to the extracellular matrix-coated membrane surface of the porous membrane 304 to form a confluent epithelial monolayer. During culture, cells (e.g., smooth muscle cells) and fibroblasts can be maintained by perfusing the upper channel and the two side lanes of the lower microchannel with epithelial and stromal media, respectively. As illustrated in FIG. 4E, vascular endothelial cells can be seeded into the side channels to form a lining of endothelial cells to mimic the function of cervical blood vessels.

FIG. 5 shows images of cervical epithelium and uterine fibroblasts at different stages of the cell culture process. As an example, feasibility of this approach was demonstrated by co-culturing human ectocervical epithelial cells with uterine fibroblasts and smooth muscle cells embedded in a type-I collagen hydrogel for up to 9 days. FIG. 5 shows phase contrast images of the confluent ectocervical epithelium (top) and uterine fibroblasts and smooth muscle cells (bottom) embedded in the stromal layer at day 3 of this example, also showing an image of epithelial cells that were stained to distinguish the percentage of live epithelial cells to dead epithelial cells. An overwhelming majority of the epithelial cells were alive at the end of day 9 of this example.

In some embodiments, to recreate a stromal-vascular interface, endothelial monolayers can be created to line the entire surfaces of the two side lanes of the lower microchannel to generate vascular compartments. Fluidic environment and delivery of soluble factors in this model can be precisely controlled by computerized perfusion pumps integrated with our cell culture device.

FIG. 6A shows an image of the exemplary microdevice introduced with lipopolysaccharides to simulate a bacterial infection in the cervix in accordance with the disclosed subject matter. In order to establish and validate a premature cervical remodeling-on-a-chip model that simulates key biophysical and biochemical alterations in the human cervical tissue during infection-induced cervical remodeling, lipopolysaccharides (LPS) or living $E. coli$ can be introduced into the epithelial compartment to simulate ascending bacterial infection in the cervix. After LPS introduction, the transport of fluorescein particles can be measured to determine barrier permeability of the microdevice due to LPS exposure.

FIG. 6B shows a graph of the results of the simulated bacterial infection in the microdevice in accordance with the disclosed subject matter. In the exemplary embodiment illustrated in FIG. 6B, three different microdevices were tested—an empty sample without a stromal gel layer, a control sample without any LPS, and a third sample with 25 micrograms of LPS/mL of solution. Resultant inflammatory responses of the cervical tissue can be used to measure cell viability, barrier permeability, activation of NFkB target gene networks, release of pro-inflammatory cytokines, changes in distribution of tight junction proteins, and endothelial expression of adhesion molecules. The example shown in FIG. 6B successfully demonstrated compromised barrier function and concomitant increases in tissue permeability due to epithelial exposure to LPS. In some embodiments, characterization of infection-induced cervical remodeling can be performed by quantitatively analyzing production of ECM proteins by fibroblasts in the stroma, mechanical stiffness of the stromal layer after tissue isolation from the microdevice, ECM architecture and structural organization, and production of matrix enzymes such as MMPs and TIMPs, among other potential outputs.

Figure 7A:
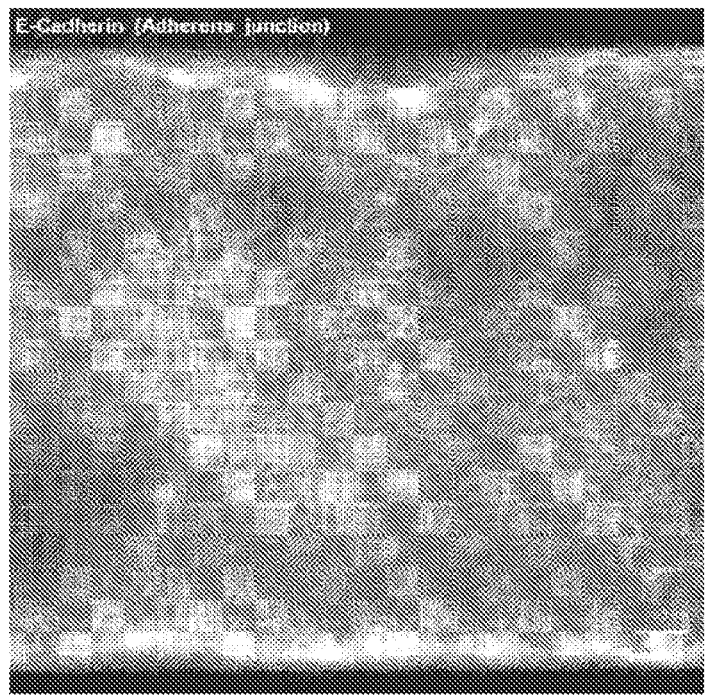
FIGS. 7A & 7B show images of junction formation in the epithelium.
Figure 7B:
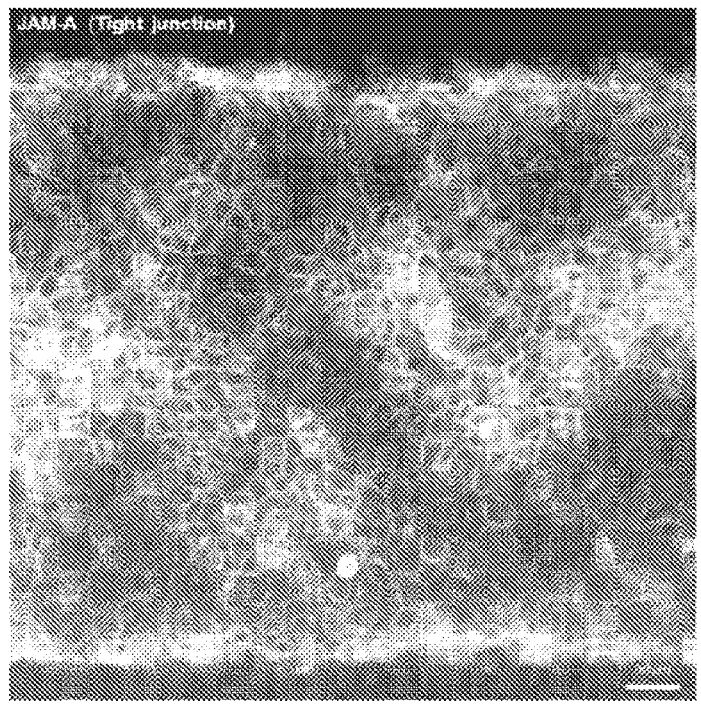

FIGS. 7A & 7B shows images of junction formation in the epithelium. FIG. 7A illustrates an example adherens junction that can be expressed and/or formed in the cervical epithelial cells of the micro-engineered models of the human cervix using the disclosed subject matter. The exemplary adherens junction of FIG. 7A can be composed of cadherin (E-Cadherin) to bind epithelial cells together to form the epithelial tissue. FIG. 7B illustrates an example tight junction that can be expressed and/or formed in the cervical epithelial cells of the micro-engineered models of the human cervix using the disclosed subject matter. Tight junctions, which can be formed using a junction adhesion molecule (e.g., JAM-A), can form an impermeable barrier, which can assist the micro-engineered model serve essential epithelial barrier functions.

Figures 8A, 8B, 8C, 8D:
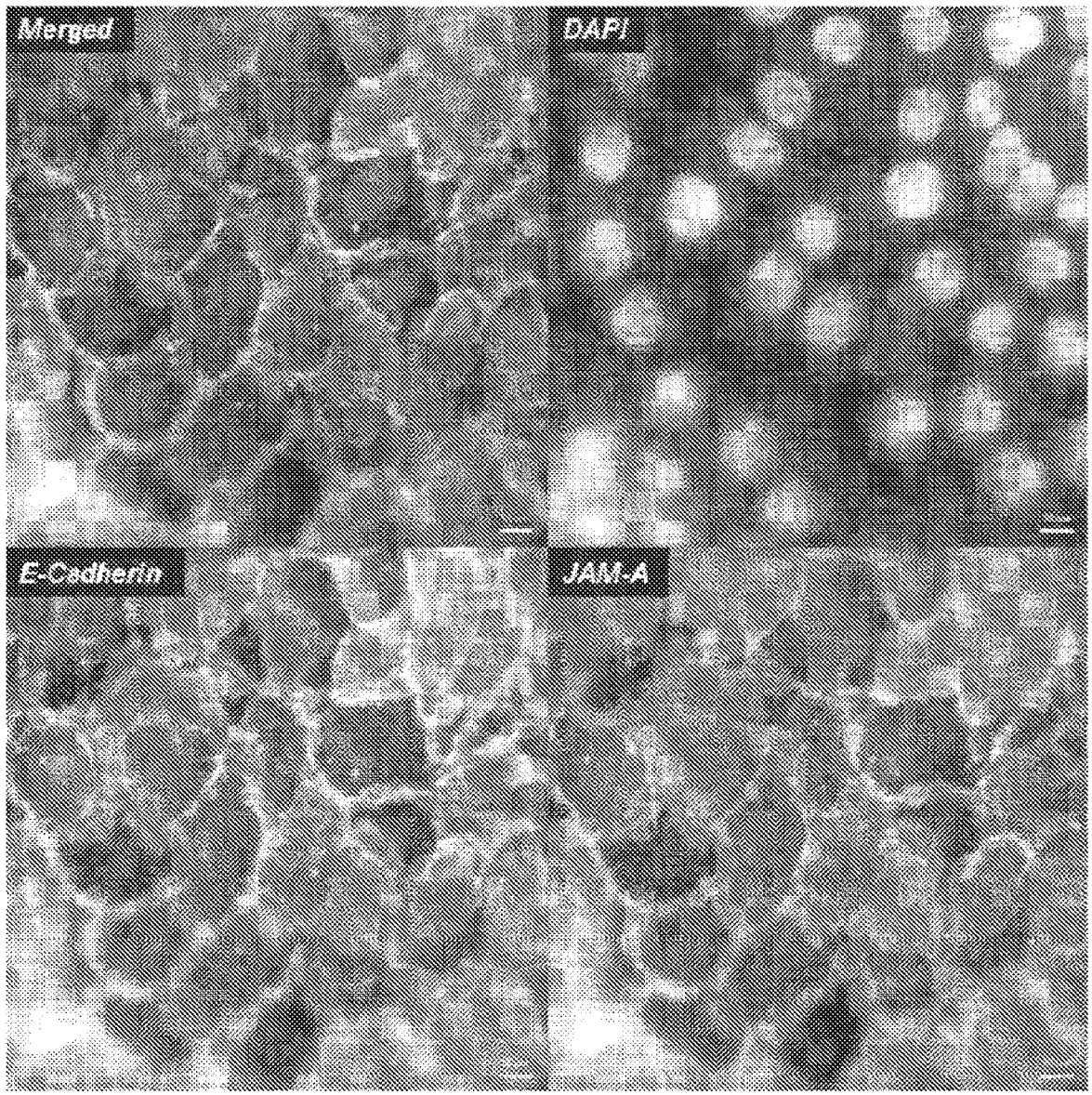
FIGS. 8A-D illustrate fluorescence microscopy images illustrating nuclei of epithelial cells, tight junctions, and adherens junctions.

FIG. 8A illustrates a merged fluorescence microscopy image illustrating nuclei of epithelial cells, tight junctions, and adherens junctions. FIG. 8B illustrates a fluorescence microscopy image illustrating nuclei of the cervical epithelial cells, in the micro-engineered models of the human cervix using the disclosed subject matter, that have been stained with a fluorescent stain that binds strongly to A-T rich regions in DNA of a cell (e.g., 4',6-diamidino-2-phenylindole, hereinafter referred to as "DAPI"). FIG. 8C illustrates adherens junctions that can be expressed and/or formed in the cervical epithelial cells of the micro-engineered models of the human cervix using the disclosed subject matter. FIG. 8D illustrates tight junctions that can be expressed and/or formed in the cervical epithelial cells of the micro-engineered models of the human cervix using the disclosed subject matter.

Figure 9:
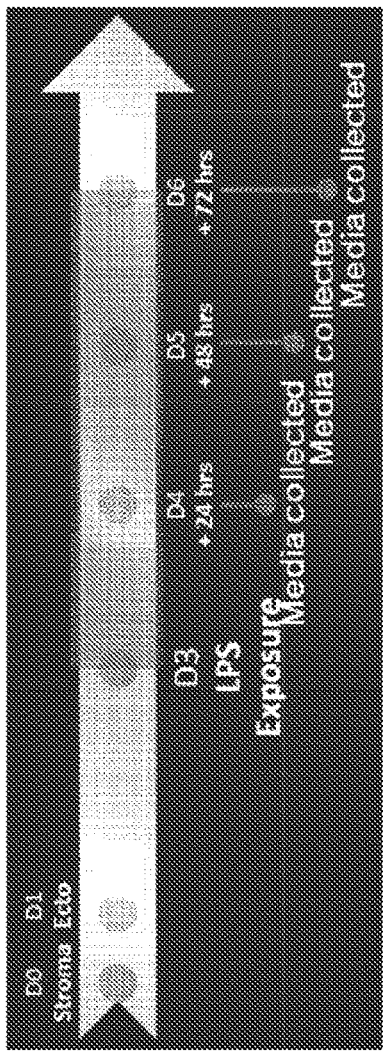
FIG. 9 illustrates a process by which secretion of cytokine from the cervical cells in the disclosed micro-engineered models of the human cervix can be measured after exposure of the cervical cells to lipopolysaccharides (LPS).

FIG. 9 illustrates a process by which secretion of cytokine from the cervical cells in the disclosed micro-engineered models of the human cervix can be measured after exposure of the cervical cells to lipopolysaccharides (LPS). In some embodiments, the cervical cells can be exposed to LPS for a predetermined amount of time (e.g., 72 hours). The conditioned media can be collected from both top (ecto) and bottom (stroma) channels at three different time points during the predetermination amount of time (e.g., at 24, 48, and 72 hours following the exposure). The level of interleukin 6 (IL-6), a cytokine that can have both a pro-inflammatory and an anti-inflammatory role, in the media can be analyzed using an enzyme-linked immunosorbent assay (ELISA), a plate-based assay technique designed for detecting and quantifying substances such as peptides, proteins, antibodies and hormones.

Figure 10:
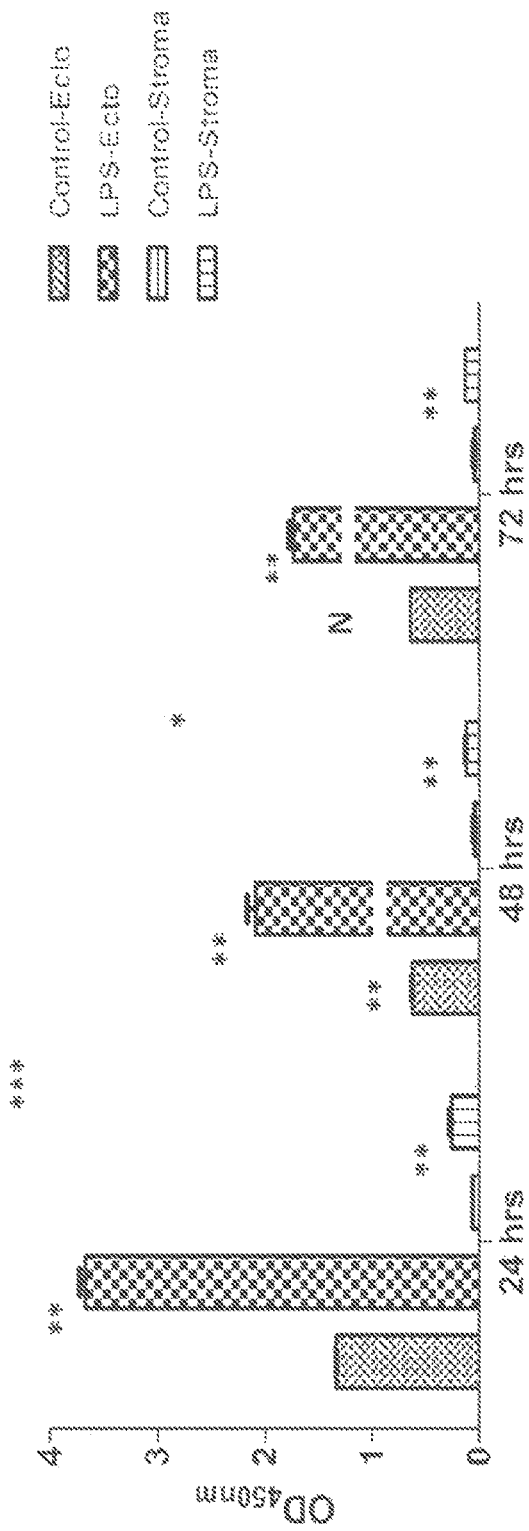
FIG. 10 illustrates exemplary measurement results of the level of IL-6 measured in response to LPS exposure of cervical cells in the disclosed micro-engineered models of the human cervix.

FIG. 10 illustrates exemplary measurement results of the level of IL-6 measured in response to LPS exposure of cervical cells in the disclosed micro-engineered models of the human cervix. As illustrated by FIG. 10, an increase of IL-6 level can be observed in both top (Ecto) and bottom (Stroma) channels in the LPS-treated group.

Figure 11:
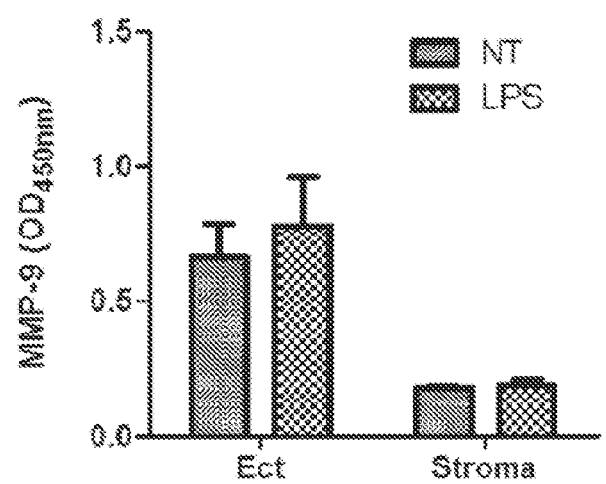
FIG. 11 illustrates exemplary measurement results of the level of collagenase involved in degradation and remodeling of ECM (e.g., MMP-9) measured in response to LPS exposure of cervical cells in the disclosed micro-engineered models of the human cervix.

FIG. 11 illustrates exemplary measurement results of the level of collagenase involved in degradation and remodeling of ECM (e.g., MMP-9) measured in response to LPS exposure of cervical cells in the disclosed micro-engineered models of the human cervix. As FIG. 11 illustrates, no significant differences can be observed between the LPS treated and non-treated (NT) control groups.

Figure 12A:
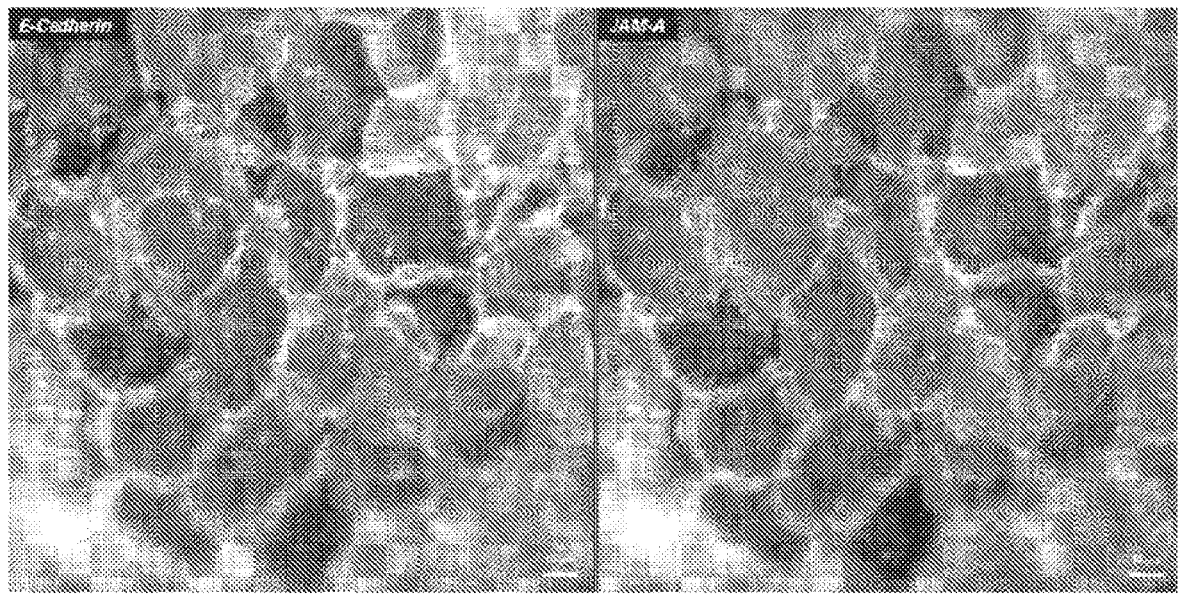
FIGS. 12A and 12B show fluroscence microsopy images of junctions formed in the cervical epithelial cells illustrating the changes in the adherens junctions and the tight junctions expressed and/or formed in the cervical epithelial cells a result of LPS exposure.
Figure 12B:
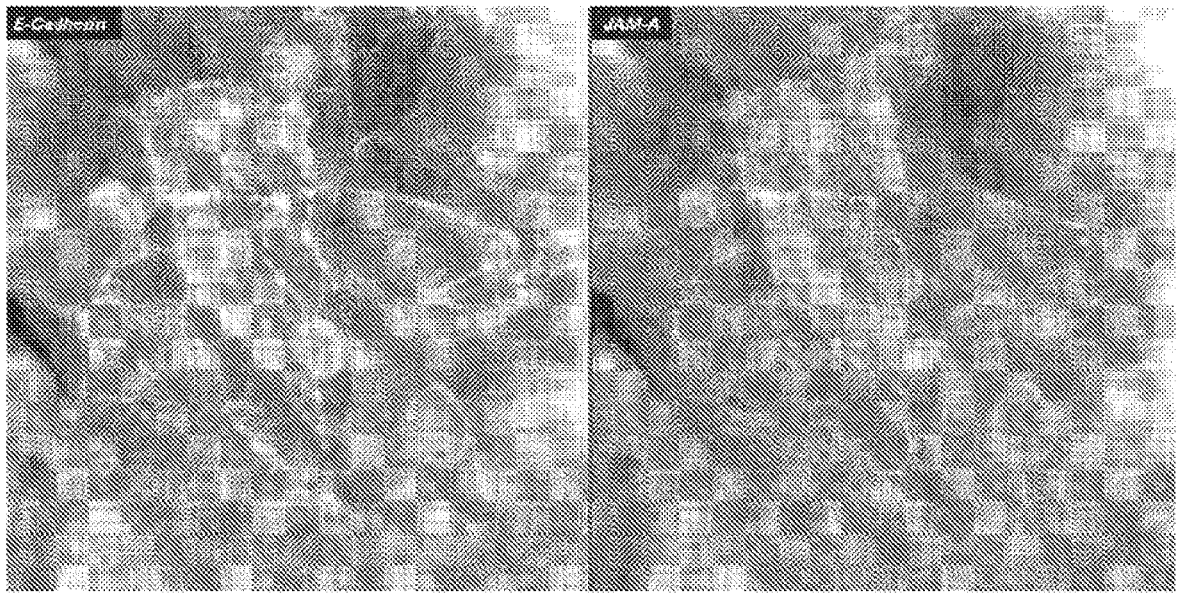

FIGS. 12A and 12B show fluroscence microsopy images of junctions formed in the cervical epithelial cells illustrating the changes in the adherens junctions and the tight junctions expressed and/or formed in the cervical epithelial cells of the micro-engineered models of the human cervix as a result of LPS exposure. FIG. 12A illustrates fluroscence microsopy images of the adherens junctions and the tight junctions expressed and/or formed in the cervical epithelial cells before the cells are exposed to LPS. FIG. 12B illustrates fluroscence microscopy images of the adherens junctions and the tight junctions expressed and/or formed in the cervical epithelial cells after the cells are exposed to LPS. As illustrated by FIGS. 12A and 12B, patterns of junction protein expressions can change after LPS exposure. For example, the junction protein expressions can become less localized between the cell borders after LPS exposure.

Figure 13A:
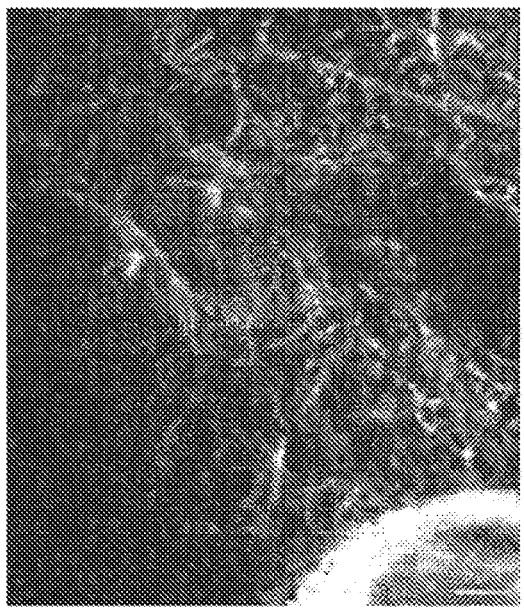
FIGS. 13A-C illustrate second harmonic generation (SHG) imaging of the stroma in in the disclosed micro-engineered models of the human cervix to visualize the collagen fibers.
Figure 13B:
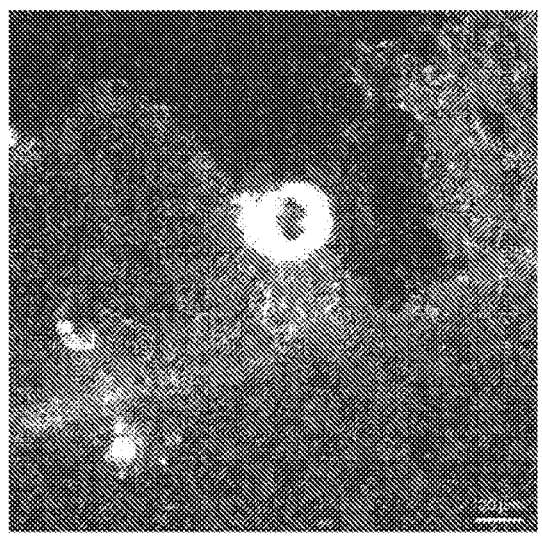
Figure 13C:
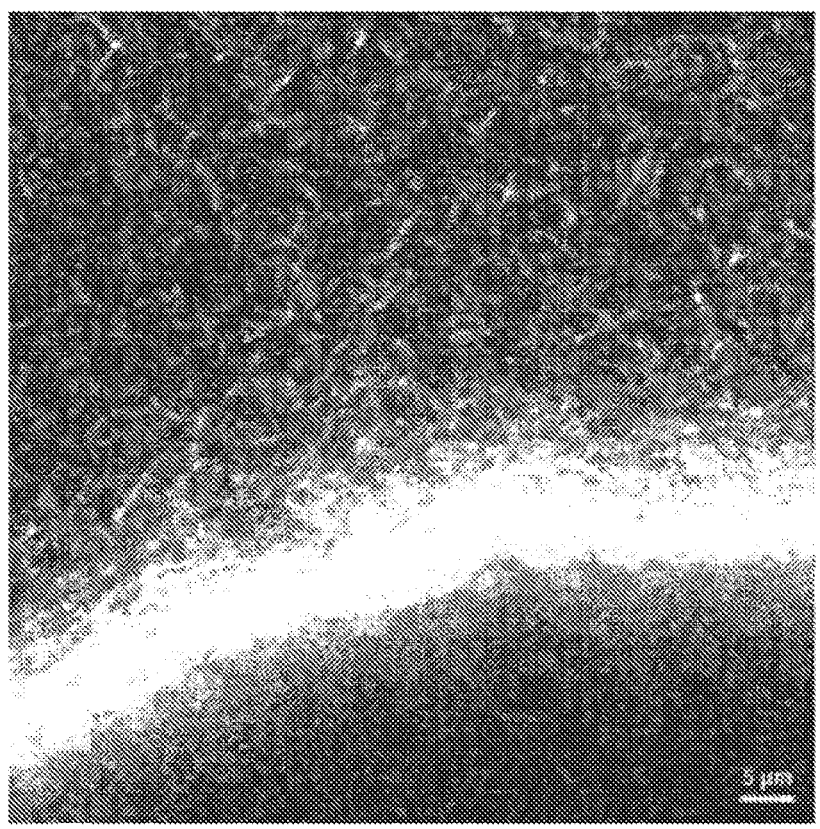

FIGS. 13A-C illustrate second harmonic generation (SHG) imaging of the stroma in the disclosed micro-engineered models of the human cervix to visualize the collagen fibers. Biomaterials such as collagen, microtubules and myosin can produce SHG signals. Fibers of collagen gel in the disclosed micro-engineered models of the human cervix can be successfully imaged with SHG imaging, as illustrated in FIGS. 13A-C. A difference in the intensity of SHG signals between the control and LPS-treated groups can also be analyzed. Additionally and/or alternatively, both control and LPS-treated micro-engineered model devices can be imaged to determine if any changes occur in the fibrous structure of the disclosed micro-engineered models of the human cervix.

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within its spirit and scope.

What is claimed is:

1. A microdevice for culturing human cervical cells, comprising:
    an upper microchannel comprising live cervical epithelial cells;
    a lower microchannel comprising:
    a first parallel lane and a second parallel lane comprising stromal media, each of the first parallel lane and the second parallel lane being and wherein the first and the second parallel lanes are lined with live vascular endothelial cells,
    a third parallel lane disposed between the first parallel lane and the second parallel lane and comprising a hydrogel comprising uterine fibroblasts and live smooth muscle cells embedded therein in hydrogel, wherein the first parallel, second parallel, and third parallel lanes of the lower microchannel are separated by
    protrusion structures disposed between the first parallel lane and the third parallel lane and between the second parallel lane and the third parallel lane, a top surface of each of the protrusion structures being offset from a top surface of the lower microchannel wherein the third parallel lane is positioned in the lower microchannel in between the first and the second parallel lanes; and
    a porous membrane positioned between the upper microchannel and the lower microchannel.

2. The microdevice of claim 1, wherein the porous membrane is configured to pass nutrients from the upper microchannel to the lower microchannel.

3. The microdevice of claim 1, wherein the upper microchannel and the lower microchannel have separate inlets through which biomaterials can be injected into the microdevice.

4. The microdevice of claim 1, wherein the protrusion structures are configured to pin menisci of a hydrogel precursor solution injected into the third parallel lane of the lower microchannel and prevent the hydrogel precursor solution from spilling into the first parallel lane and the second parallel lane.

5. The microdevice of claim 1, wherein the live cervical epithelial cells in the upper microchannel are perfused with epithelial media and wherein the live vascular endothelial cells in the lower microchannel are perfused with the stromal media in the first parallel lane and the second parallel lane.

6. A method of manufacturing a microdevice for culturing human cervical cells, comprising:
    injecting hydrogel precursor solution comprising cervical stromal cells into the third parallel lane of the lower microchannel of the microdevice of claim 1;
    injecting human cervical epithelial cells into the upper microchannel of the microdevice, resulting in an extracellular membrane coated surface of at least one epithelial monolayer;
    perfusing the first parallel lane and the second parallel lane of the lower microchannel with stromal media; and seeding vascular endothelial cells into the first parallel lane and the second parallel lane to form a lining of endothelial cells.

7. The method of claim 6, wherein the hydrogel precursor solution injected into the third parallel lane is allowed to solidify into a hydrogel before injecting the human cervical epithelial cells into the upper microchannel.

8. A microdevice, comprising:
an upper microchannel;
a lower microchannel comprising:
a first parallel lane and a second parallel lane, each of the first parallel lane and the second parallel lane being lined with live vascular endothelial cells;
a third parallel lane disposed between the first parallel lane and the second parallel lane and comprising a hydrogel comprising cells therein; and
protrusion structures disposed between the first parallel lane and the third parallel lane and between the second parallel lane and the third parallel lane, a top surface of each of the protrusion structures being offset from a top surface of the lower microchannel; and
a porous membrane positioned between the upper microchannel and the lower microchannel.

9. The microdevice of claim 8, wherein the porous membrane is configured to pass nutrients from the upper microchannel to the lower microchannel.

10. The microdevice of claim 8, wherein the upper microchannel and the lower microchannel have separate inlets through which biomaterials can be injected into the microdevice.

11. The microdevice of claim 8, wherein the protrusion structures are configured to pin menisci of a hydrogel precursor solution injected into the third parallel lane of the lower microchannel and prevent the hydrogel precursor solution from spilling into the first parallel lane and the second parallel lane.

12. The microdevice of claim 8, wherein the upper microchannel comprises live cervical epithelial cells.

13. The microdevice of claim 8, wherein the hydrogel comprises uterine fibroblasts and live smooth muscle cells embedded therein.

* * * * *

UNITED STATES PATENT AND TRADEMARK OFFICE
CERTIFICATE OF CORRECTION

| | | |
|---|---|---|
| PATENT NO. | : 11,920,116 B2 | Page 1 of 1 |
| APPLICATION NO. | : 17/352015 | |
| DATED | : March 5, 2024 | |
| INVENTOR(S) | : Dongeun Huh et al. | |

It is certified that error appears in the above-identified patent and that said Letters Patent is hereby corrected as shown below:

In the Specification

Under Column no. 1, Line no. 8, Replace:
"This application is related to,"
With:
--This application is a continuation of U.S. Patent Application Ser. No. 15/769,387, filed Apr. 19, 2018, which is a U.S. National Stage Patent Application under 35 U.S.C. § 371 of International Application No. PCT/US2016/058220, filed on Oct. 21, 2016, which is related to,--

Under Column no. 1, Line no. 9, Replace:
"Provisional Patent"
With:
--U.S. Provisional Patent--

Under Column no. 1, Line no. 12, Replace:
"contents of which is incorporated"
With:
--contents of each of which are incorporated--

Under Column no. 1, Line no. 13, Replace:
"herein."
With:
--herein in their entirety.--

Signed and Sealed this
Ninth Day of July, 2024

Katherine Kelly Vidal
*Director of the United States Patent and Trademark Office*